United States Patent [19]
Koeda et al.

[11] Patent Number: 5,924,978
[45] Date of Patent: Jul. 20, 1999

[54] PORTABLE ENDOSCOPE SYSTEM WITH A BAYONET SWITCHING MECHANISM.

[75] Inventors: Takashi Koeda; Hiroshi Sano; Hirohisa Ueda; Kunitoshi Ikeda; Kunikiyo Kaneko; Rensuke Adachi, all of Tokyo, Japan

[73] Assignee: Asahi Kogaku Kogyo Kabushiki Kaisha, Tokyo, Japan

[21] Appl. No.: 08/681,532

[22] Filed: Jul. 23, 1996

[30] Foreign Application Priority Data

Aug. 4, 1995 [JP] Japan ..................... 7-199650
Oct. 4, 1995 [JP] Japan ..................... 7-257328

[51] Int. Cl.$^6$ ........................................... A61B 1/06
[52] U.S. Cl. .................. 600/178; 600/131; 600/180; 600/199; 600/200
[58] Field of Search ................... 600/178–180, 600/199, 200, 131; 439/311, 312, 314, 315, 318, 319; 307/66, 150

[56] References Cited

U.S. PATENT DOCUMENTS

| | | | |
|---|---|---|---|
| 2,400,351 | 5/1946 | Hart | 439/314 |
| 3,315,207 | 4/1967 | Speelman | 600/139 |
| 3,586,424 | 6/1971 | Schenk | 351/213 |
| 3,919,538 | 11/1975 | Yata | 439/318 |
| 4,065,710 | 12/1977 | Zytka | 320/2 |
| 4,433,675 | 2/1984 | Konoshima | 600/178 |
| 4,574,783 | 3/1986 | Kazuhiro et al. | 600/132 |
| 4,580,198 | 4/1986 | Zinnanti, Jr. | 362/203 |
| 4,583,528 | 4/1986 | Bauman | 600/178 |
| 4,652,094 | 3/1987 | Kitajima | 359/375 |
| 4,911,148 | 3/1990 | Sosnowski et al. | 600/193 |
| 5,184,603 | 2/1993 | Stone | 600/193 |
| 5,428,699 | 6/1995 | Pon | 600/108 |

*Primary Examiner*—Gene Mancens
*Assistant Examiner*—Ira Hatton
*Attorney, Agent, or Firm*—Greenblum & Bernstein, P.L.C.

[57] ABSTRACT

A portable endoscope having a control part containing an entrance end portion of a light guide for transmitting light for illuminating an object, and an illuminating light supply unit containing a light source lamp for supplying illuminating light to the light guide. A connecting mechanism detachably connects the control part and the light supply unit. A switch for turning on/off the light source lamp is provided in the connecting mechanism. When the light supply unit is connected to the control part in a predetermined state, the switch is turned on; when the former is detached from the latter, the switch is turned off. An electric resistor may be provided for gradually reducing the electric resistance between the lamp and a power supply therefor from a high-resistance state to a low-resistance state as the switch is moved from an OFF position toward an ON position.

10 Claims, 15 Drawing Sheets

5,924,978

PORTABLE ENDOSCOPE SYSTEM WITH A BAYONET SWITCHING MECHANISM.

BACKGROUND OF THE INVENTION

The present disclosure relates to subject matter contained in Japanese Patent Application No. 7-199650 (filed on Aug. 4, 1995) and Japanese Patent Application No. 7-257328 (filed on Oct. 4, 1995), which are expressly incorporated herein by reference in their entireties.

1. Field of the Invention

The present invention relates to a portable endoscope having an illuminating light supply unit which contains a light source lamp for supplying illuminating light to a light guide.

2. Description of the Prior Art

A conventional portable endoscope has a light-emitting device for illumination which is provided in an endoscope control part. In general, such a portable endoscope has an illuminating light supply unit which contains a light source lamp and a power supply for the lamp, e.g. a dry battery, and the illuminating light supply unit is detachably connected to the control part. ON/OFF control of the light source lamp is effected using a manual switch which is provided on the illuminating light supply unit.

However, in a case where the light source lamp is turned ON/OFF with a manual switch provided on the illuminating light supply unit, the light source lamp may be left in the ON state when it is not needed, causing battery power to be wasted.

Particularly, if the operator forgets to turn OFF the switch when the illuminating light supply unit is detached from the endoscope control part after the use of the endoscope, there are cases where the battery has run down before the operator realizes it, and hence, the light source lamp cannot be lit up when the endoscope is used for a subsequent endoscopic inspection (endoscopy).

In addition, the illuminating light supply unit that is connected directly to the control part of the endoscope must be arranged to be as compact and lightweight as possible in order to prevent the illuminating light supply unit from impairing the controllability of the endoscope.

The switch that is used to turn ON/OFF the light source lamp is a switch which merely performs ON/OFF control. Therefore, it is likely that the light source lamp will be burned out by an inrush current that flows when the switch is turned ON to light the light source lamp.

Particularly, when a rechargeable secondary battery is used as a power supply, the power supply voltage may exceed the rated value immediately after the battery has been charged. When an AC/DC adapter is used as a power supply, a voltage drop is less likely to occur when the power is turned ON than in the case of a battery. Therefore, in these cases, the light source lamp is likely to be burned out by an inrush current.

SUMMARY OF THE INVENTION

An object of the present invention is to provide a portable endoscope in which a light source lamp is surely turned OFF when an illuminating light supply unit is detached from the control part of the endoscope.

Another object of the present invention is to provide a portable endoscope which is capable of reducing an inrush current flowing when the power is turned ON to light a light source lamp which is provided in a compact and lightweight illuminating light supply unit connected to the endoscope.

Other objects and advantages of the present invention will become apparent from the following detailed description of illustrated embodiments of the invention.

According to the present invention, there is provided a portable endoscope having a control part containing an entrance end portion of a light guide for transmitting light for illuminating an object, and an illuminating light supply unit containing a light source lamp for supplying illuminating light to the light guide. The portable endoscope includes a connecting mechanism for detachably connecting the control part and the illuminating light supply unit. A switch for turning ON/OFF the light source lamp is provided in the connecting mechanism. When the illuminating light supply unit is connected to the control part in a predetermined state, the switch is turned ON, whereas, when the illuminating light supply unit is detached from the control part, the switch is turned OFF.

In addition, there is provided a portable endoscope having a control part in which an entrance end portion of a light guide for transmitting light for illuminating an object is disposed, and an illuminating light supply unit containing a light source lamp for supplying illuminating light to the light guide. The portable endoscope includes a switch provided in the illuminating light supply unit to turn ON/OFF the light source lamp, and an electric resistor for gradually reducing an electric resistance between the light source lamp and a power supply for the lamp from a high-resistance state to a low-resistance state as the switch is moved from an OFF position toward an ON position.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
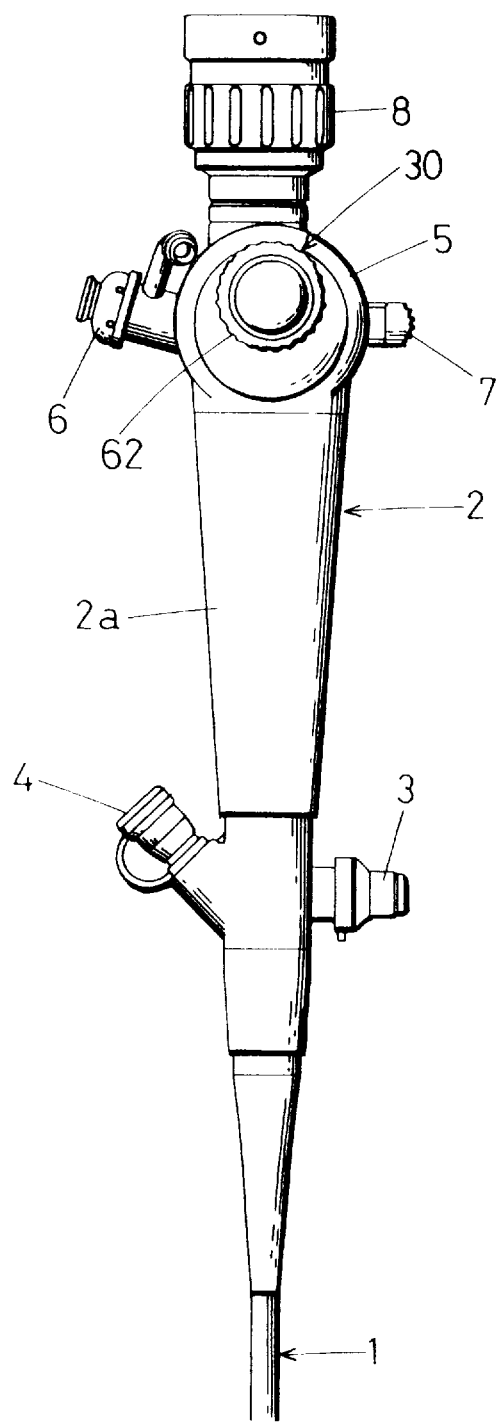
FIG. 1 is a side view of a portable endoscope according to a first embodiment of the present invention.
Figure 2:
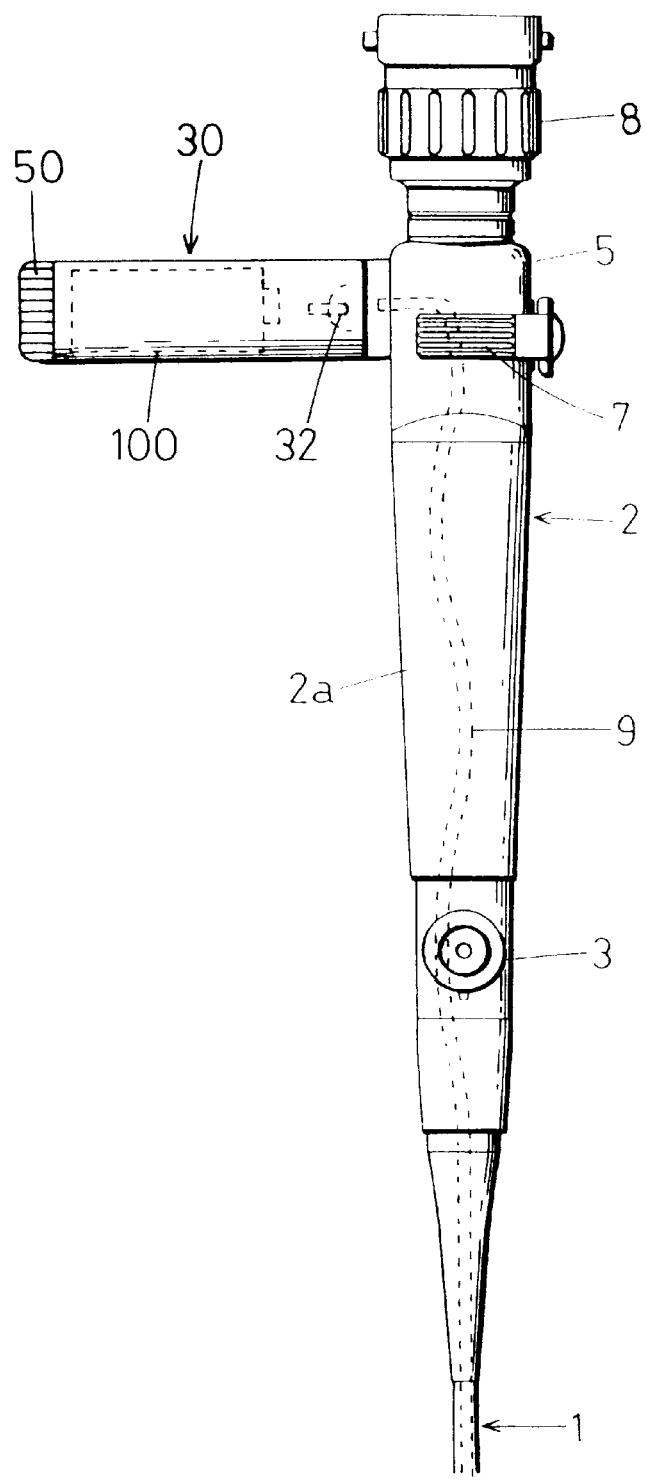
FIG. 2 is a rear view of the portable endoscope according to the first embodiment of the present invention.

FIG. 1 is a side view of a portable endoscope according to a first embodiment of the present invention, particularly showing a control part 2 of the endoscope. FIG. 2 is a rear view of the portable endoscope. The portable endoscope has an insert part 1 which is armored with a flexible tube. A proximal end of the insert part 1 is connected to a lower end portion of the control part 2.

About three fourths from the bottom of the control part 2 is a grip portion 2a. A forceps inlet 4 is provided between the grip portion 2a and the insert part 1 so as to project obliquely forward. A pressure control valve 3 is used to control pressure in the endoscope, which is formed into an airtight structure.

The control part 2 has a control mechanism portion 5 above a grip portion 2a. The control mechanism portion 5 has a suction control valve 6 which is disposed on a front side thereof to carry out a suction operation through a forceps channel (not shown) inserted in the insert part 1. A control mechanism portion 5 further has a bending control lever 7 which is disposed on a rear side thereof to effect a bending control of a remote-controlled bendable portion (not shown) which is formed at a distal end of the insert part 1. In addition, an eyepiece 8 is provided on a top of the control mechanism portion 5.

A light guide fiber bundle 9, for transmitting light for illuminating an object, has an entrance end portion thereof disposed in the control mechanism portion 5, and extends through the insert part 1 and the grip portion 2a of the control part 2. The exit end portion of the light guide fiber bundle 9 is disposed in the distal end of the insert part 1.

An illuminating light supply unit 30 for supplying illuminating light to the light guide fiber bundle 9 is detachably connected to a side of the control mechanism portion 5. A bayonet mount (described later) is used as a mechanism for detachably connecting the illuminating light supply unit 30 to the control mechanism portion 5.

The illuminating light supply unit 30 contains a light source lamp 32 that emits illuminating light which is to be supplied to the light guide fiber bundle 9, and a battery 100 (or the like) which serves as a power supply for illuminating the light source lamp 32. The battery 100 may be any type of battery, e.g. a dry battery or a rechargeable nickel-cadmium battery.

The battery 100 can be replaced by removing a cap 50 which is detachably attached to the outer end of the illuminating light supply unit 30. An AC/DC adapter (or the like) may be connected to the illuminating light supply unit 30 in place of the battery 100.

Figure 3:
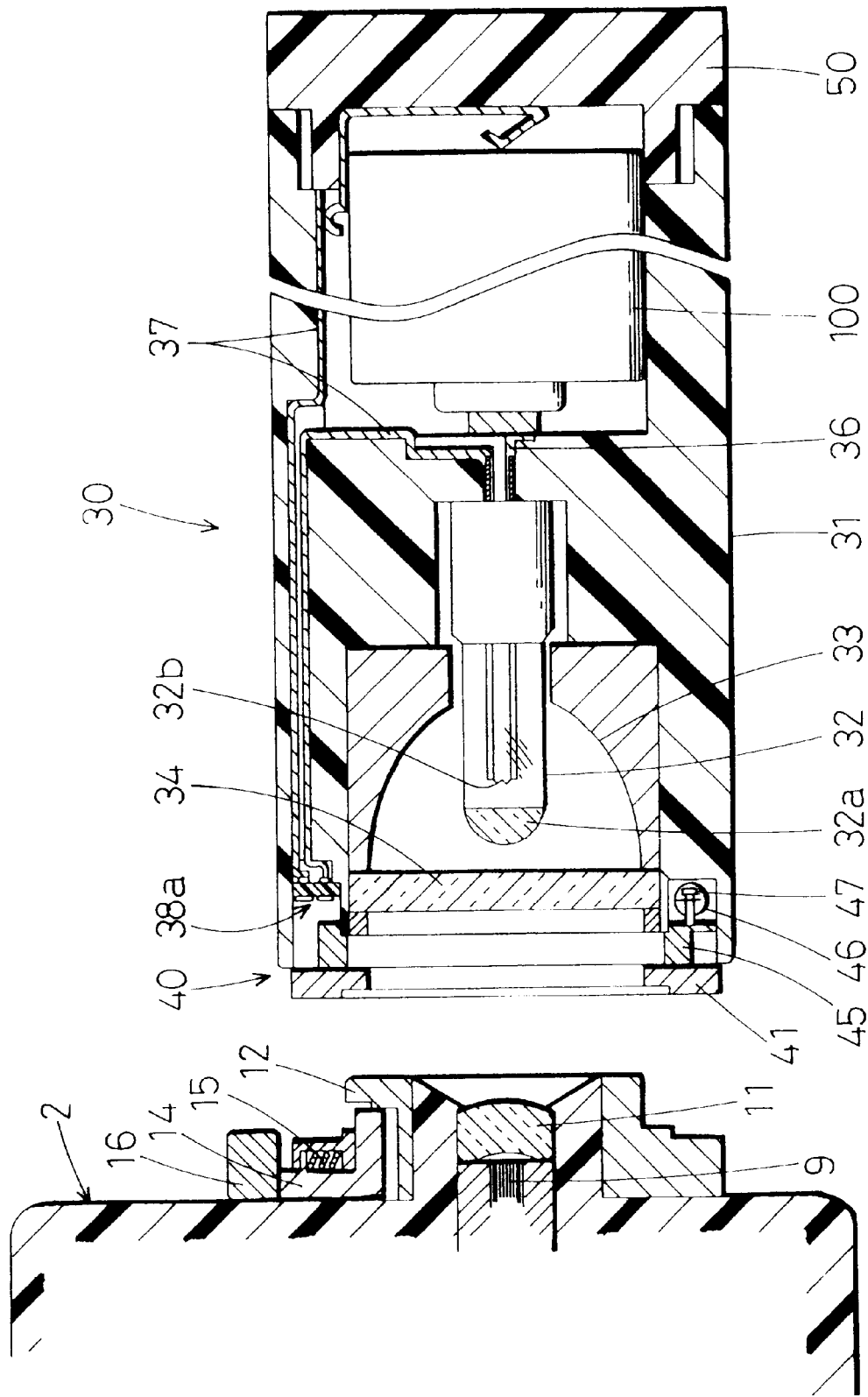
FIG. 3 is a sectional side view showing the first embodiment of the present invention with an illuminating light supply unit detached from an endoscope control part.
Figure 4:
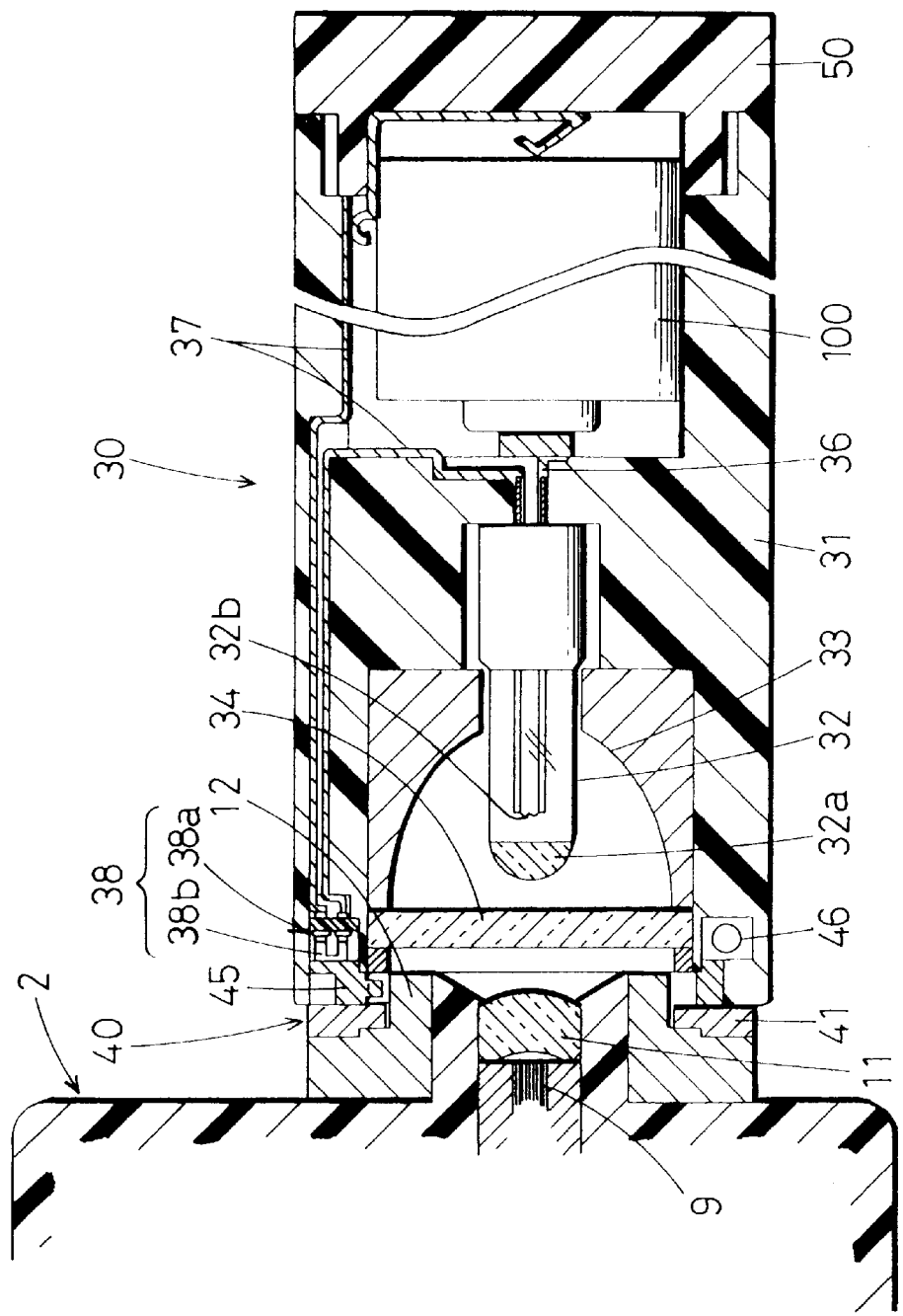
FIG. 4 is a sectional side view showing the first embodiment of the present invention with the illuminating light supply unit connected to the endoscope control part.

FIGS. 3 and 4 show a joint between the illuminating light supply unit 30 and the control part 2. FIG. 3 shows a state where the illuminating light supply unit 30 is detached from the control part 2. FIG. 4 shows a state where the illuminating light supply unit 30 is connected to the control part 2.

A convex meniscus lens 11 is disposed in the control part 2 so as to face an entrance end surface of the light guide fiber bundle 9. As shown in the front view of FIG. 5, three bayonet inner projections 12 are fixedly provided on the control part 2 at respective positions which are circumferentially spaced on an imaginary circle centered at an optical axis of the convex meniscus lens 11.

Figure 5:
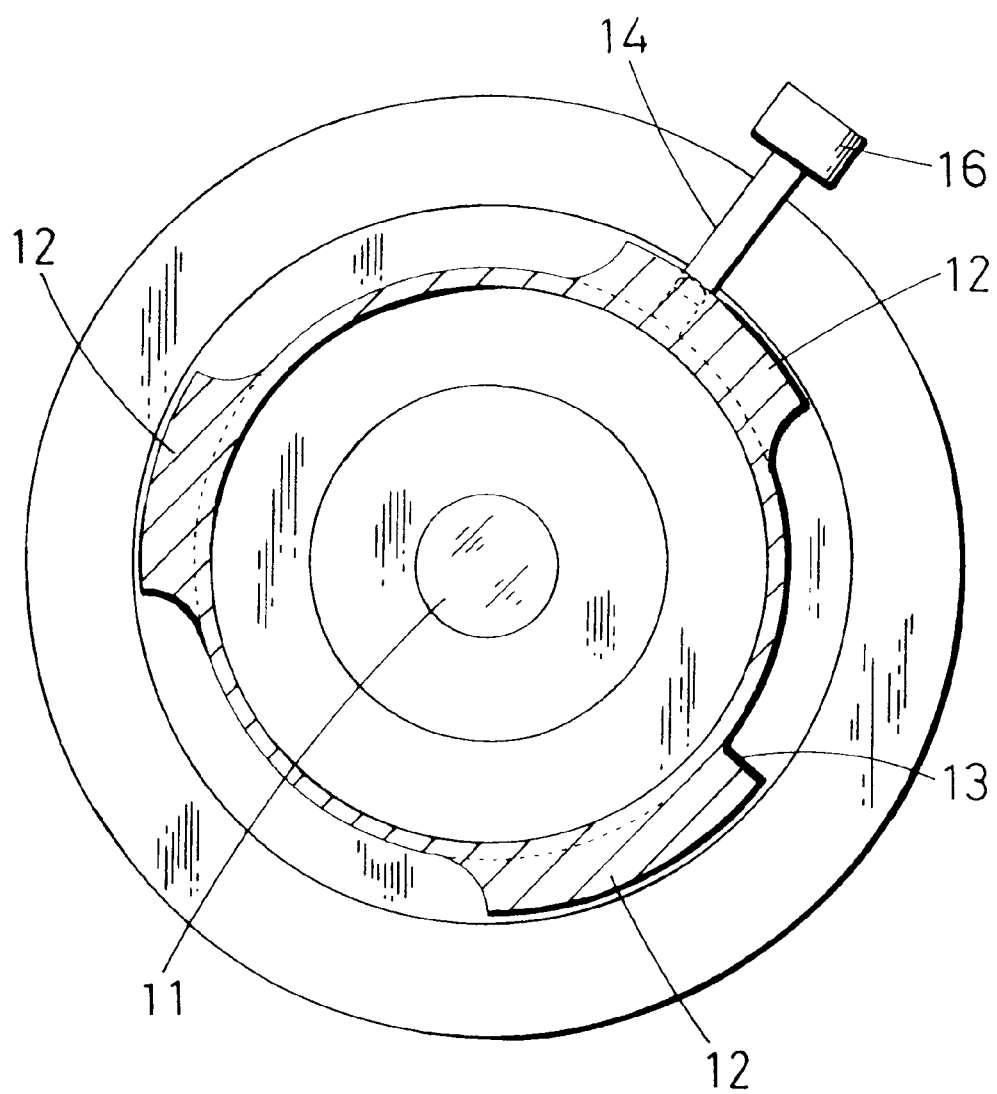
FIG. 5 is a front view of a bayonet mount portion provided on the control part in the first embodiment of the present invention.

A side end of one of the bayonet inner projections 12 is used as a driving end 13 for circumferentially pushing a rotating ring 45 (described later) to rotate. In FIG. 5, the bayonet inner projections 12 are hatched with a view to clarify the configuration thereof.

A lock pin 14 is biased outwardly by a helical compression spring 15 for locking the illuminating light supply unit 30 in a connected position. Usually, as shown in FIG. 3, the lock pin 14 is in a lock position, which is an outer position. The lock pin 14 can be moved to an unlock position, which is an inner position, by pressing a lock button 16 attached to the head of the lock pin 14.

The illuminating light supply unit 30 has a casing 31. The casing 31 contains a light source lamp 32 at the distal end thereof (which is to be connected to the control part 2). A miniature bulb is used as the light source lamp 32. The light source lamp 32 has a convex lens 32a formed at a distal end thereof.

A spheroidal mirror 33 is placed such that a filament 32b of the light source lamp 32 lies at a focal point of the spheroidal mirror 33, thereby allowing illuminating light emitted from the light source lamp 32 to converge near the entrance end portion of the light guide fiber bundle 9 and to enter it. A transparent cover glass 34 is attached to the opening end of the spheroidal mirror 33.

The battery 100 is contained in the casing 31 at the back of the light source lamp 32. A cap 50 is engaged with the rear end portion of the casing 31. The battery 100 can be pulled out of the casing 31 for replacement by disengaging the cap 50 from the rear end portion of the casing 31.

Two electrodes project rearwardly from the base portion of the light source lamp 32. One of the two electrodes is electrically connected to the positive electrode of the battery 100 through a positive-electrode conducting path 36.

The other electrode of the light source lamp 32 is electrically connected to the negative electrode of the battery 100 through a negative-electrode conducting path 37. The negative-electrode conducting path 37 is divided into two parts at an intermediate portion thereof, and these two parts are connected to a pair of contacts 38a of a switch 38 at the intermediate portion of the negative-electrode conducting path 37.

Accordingly, when the switch 38 is turned ON, the light source lamp 32 is lit up by electrical energy supplied from the battery 100. When the switch 38 is turned OFF, the battery 100 and the light source lamp 32 are electrically disconnected, and thus the light source lamp 32 is turned OFF.

The switch 38 is provided in a bayonet mount mechanism 40 which is attached to the distal end portion of the casing 31. The negative-electrode conducting path 37 is connected to a pair of contacts 38a which are disposed in parallel with a slight gap provided therebetween such that the contacts 38a do not electrically contact each other.

Figure 6:
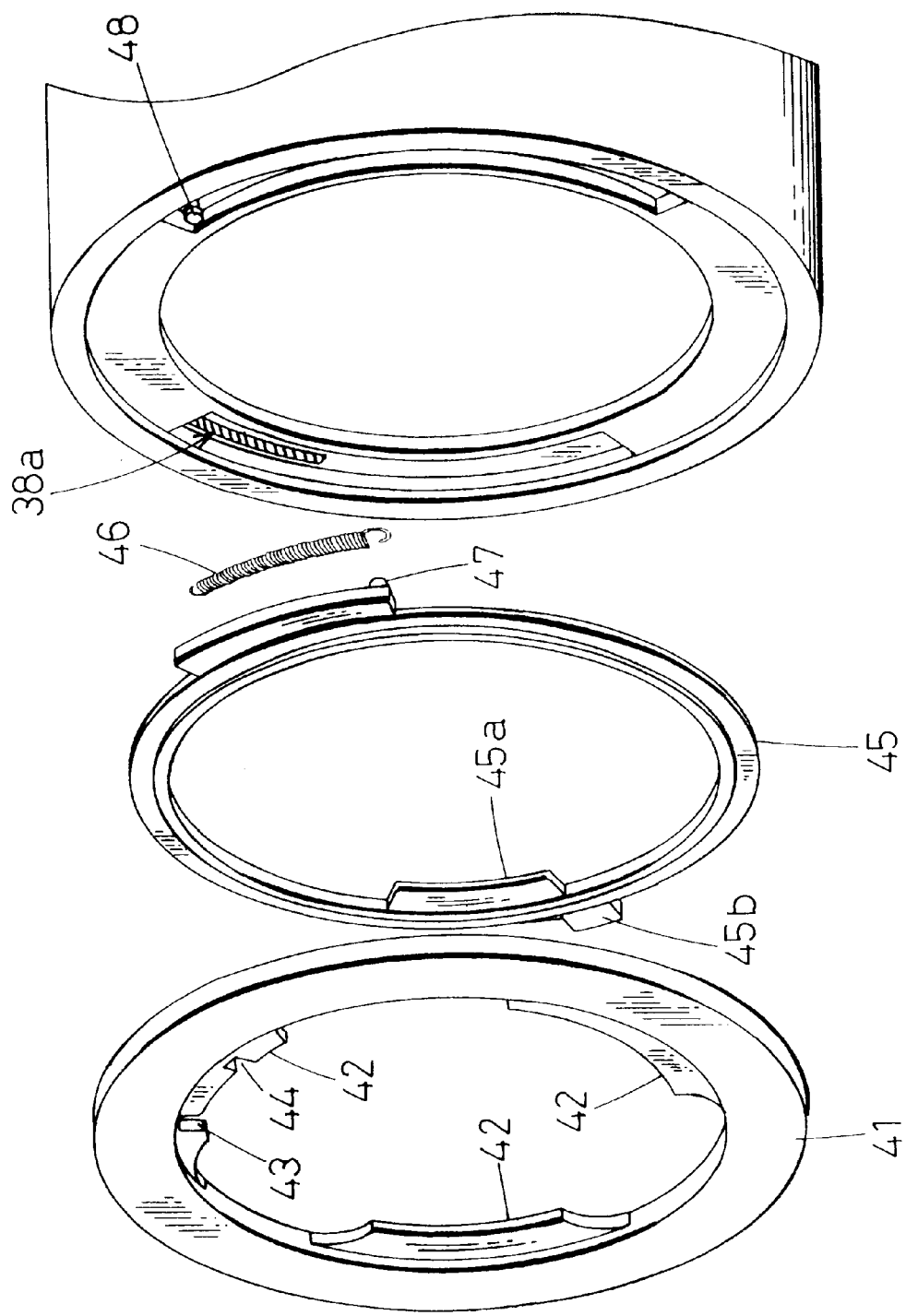
FIG. 6 is a perspective view of a bayonet mount portion provided on the illuminating light supply unit in the first embodiment of the present invention.

FIG. 6 shows the bayonet mount mechanism 40 in which a switch 38 is incorporated as described above. A bayonet mount plate 41 is fixed to the foremost end portion of the bayonet mount mechanism 40. The bayonet mount plate 41 has a configuration corresponding to the bayonet inner projections 12 provided on the control part 2.

Figure 7:
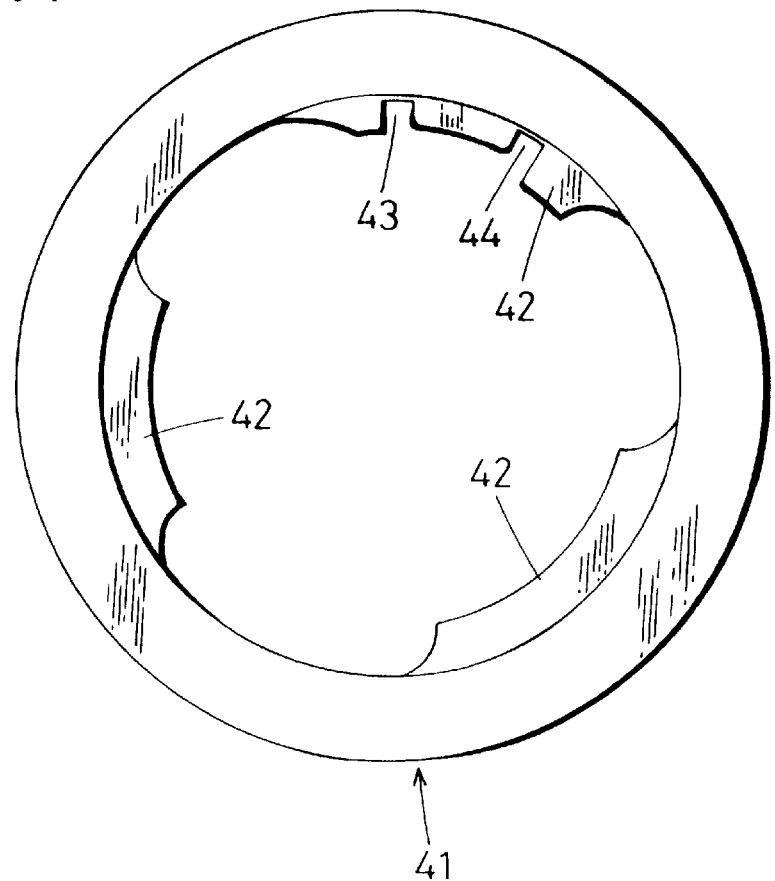
FIG. 7 is a front view of a bayonet mount plate in the first embodiment of the present invention.

As shown in FIG. 7, the bayonet mount plate 41 has three bayonet outer projections 42 which are formed such that the bayonet inner projections 12 just pass through corresponding spaces defined between the adjacent bayonet outer projections 42. The bayonet mount plate 41 further has a first and second lock grooves 43 and 44 in which the lock pin 14 engages.

Referring to FIG. 6, a rotating ring 45 is disposed behind the bayonet mount plate 41. The rotating ring 45 is rotatable in an annular recess which is formed in the distal end surface of the casing 31 over the entire circumference. The rotating ring 45 is biased in a direction for returning to a standby position by a helical tension spring 46. Two ends of the helical tension spring 46 are respectively engaged with a pin 47 projecting from the rear side of the rotating ring 45 and with a pin 48 projecting from the bottom of the recess in the distal end of the casing 31.

A drive receiving projection 45a projects from the inner periphery of the rotating ring 45 such that the driving end 13 of one bayonet inner projection 12 can abut on the drive receiving projection 45a. When the bayonet inner projections 12 are inserted into the bayonet mount mechanism 40 and rotated, the drive receiving projection 45a is pushed by the driving end 13 of one bayonet inner projection 12, causing the rotating ring 45 to rotate while expanding the helical tension spring 46.

Figure 8:
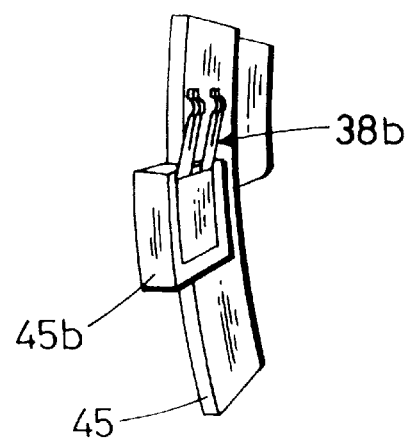
FIG. 8 is a perspective view of a conducting brush in the first embodiment of the present invention.

A projection 45b projects from the outer periphery of the rotating ring 45. As shown in FIG. 8, a conducting brush 38b is mounted on the projection 45b. The conducting brush 38b electrically connects the two parts of the negative-electrode conducting path 37 by simultaneously contacting the pair of contacts 38a of the switch 38.

However, when the illuminating light supply unit 30 is separate from the endoscope control part 2, the conducting brush 38b and the contacts 38a are separate from each other because the rotating ring 45 is constantly biased by the helical tension spring 46 in a direction in which the conducting brush 38b comes away from the contacts 38a. Accordingly, when the illuminating light supply unit 30 is detached from the control part 2, the switch 38 is always OFF, and hence the light source lamp 32 is in an OFF state.

In this embodiment, arranged as described above, when the portable endoscope is to be used, the illuminating light supply unit 30, which is detached from the control part 2 as shown in FIG. 3, is fitted to the control part 2 in such a manner that the bayonet inner projections 12 provided on the control part 2 are inserted into the spaces between the bayonet outer projections 42 provided on the illuminating light supply unit 30.

Figure 9:
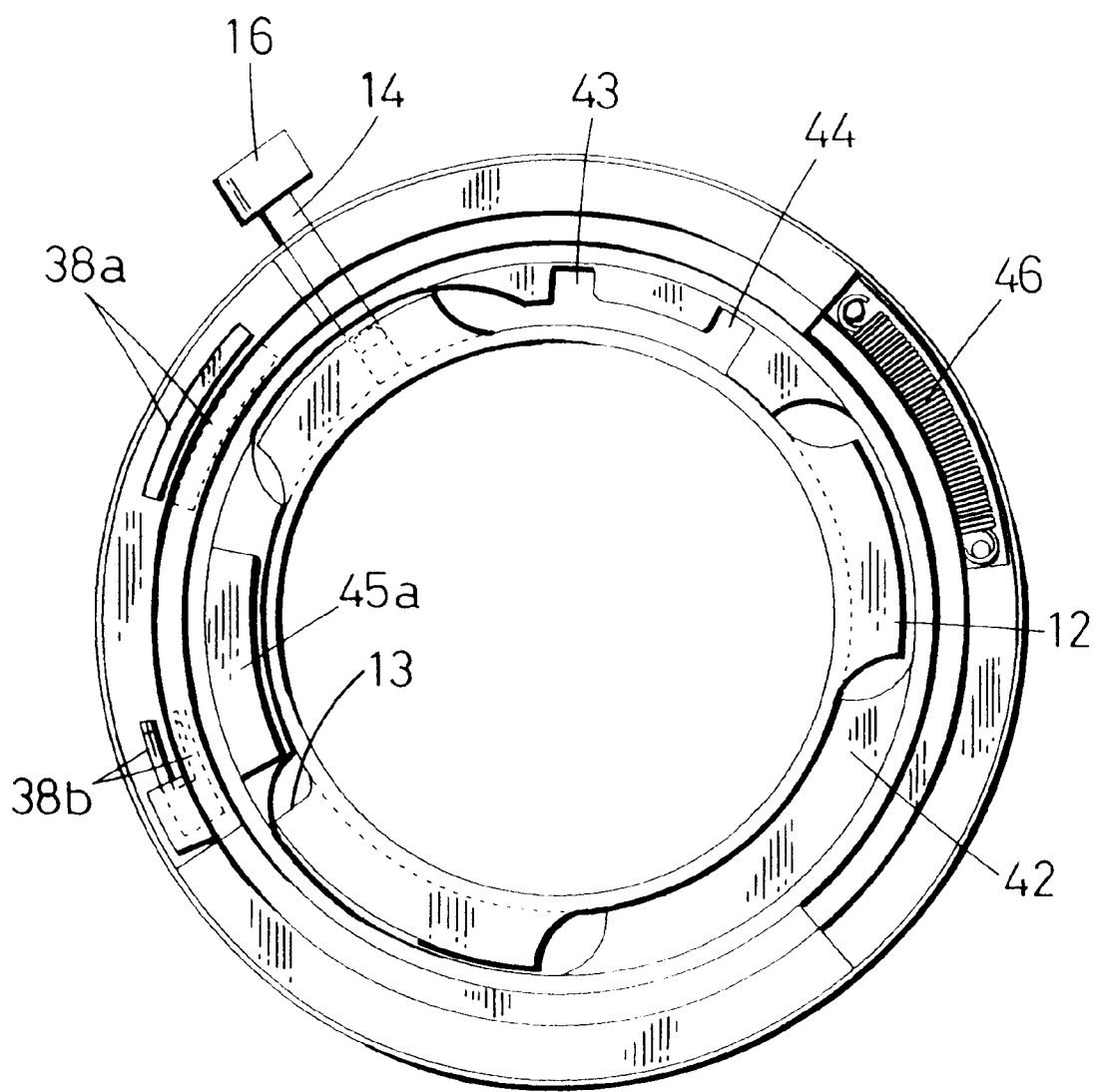
FIG. 9 is a partly-cutaway front view showing a bayonet mount in the first embodiment of the present invention in a state where the bayonet mount is being engaged.

Consequently, the bayonet inner projections 12 pass through the bayonet mount plate 41, and as shown in FIG. 9, the bayonet inner projections 12 lie in the same plane as the rotating ring 45.

Figure 10:
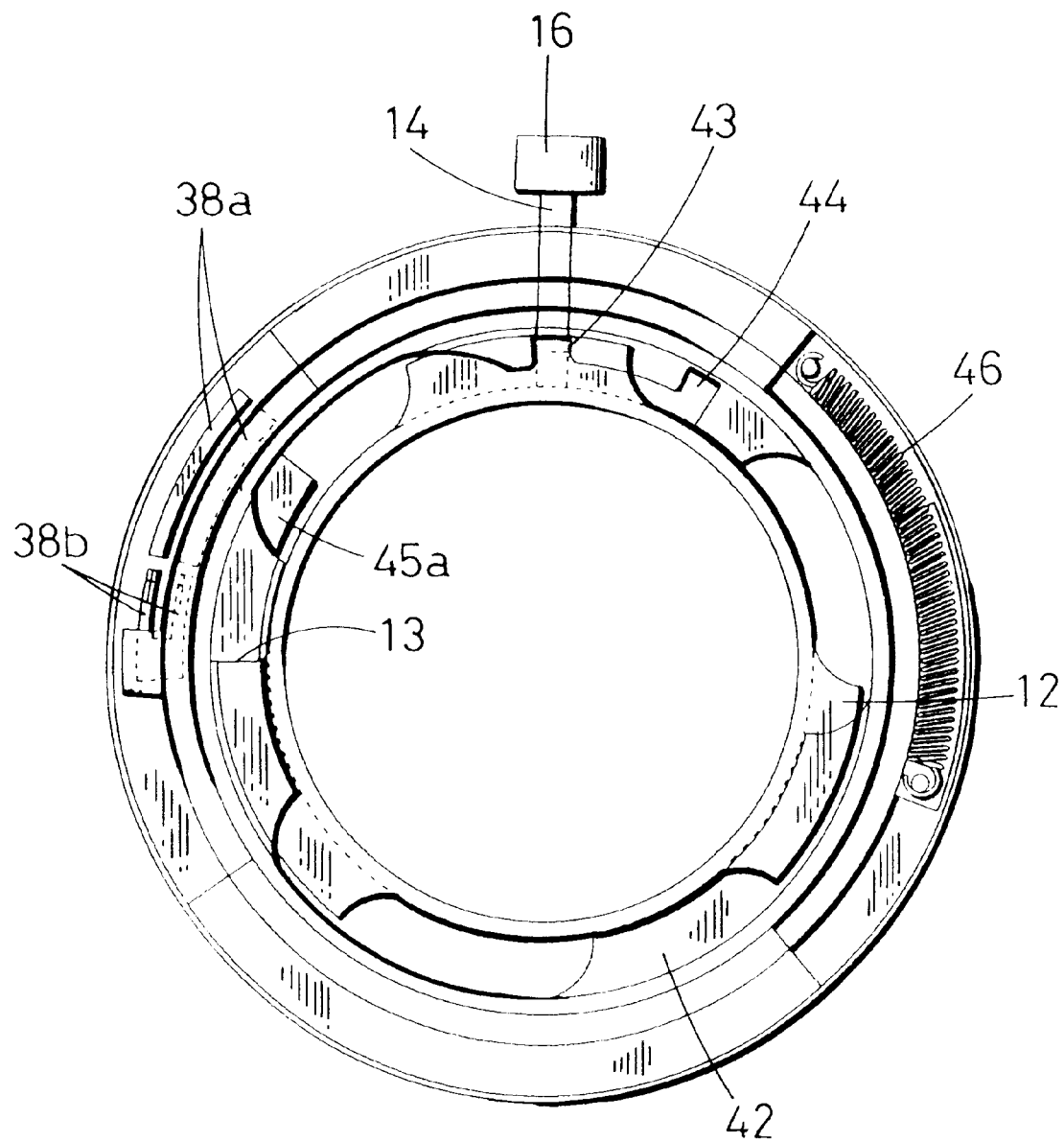
FIG. 10 is a partly-cutaway front view showing the bayonet mount which in an engaged position in a switch-OFF state in the first embodiment of the present invention.

Then, the illuminating light supply unit 30 is rotated about its own axis. As a result, as shown in FIG. 10, the bayonet inner projections 12 engage with the rear sides of the corresponding bayonet outer projections 42 to a certain extent, thereby allowing the illuminating light supply unit 30 to be connected to the control part 2. In this position, the lock pin 14 engages in the first lock groove 43 to stop rotation of the illuminating light supply unit 30, thereby locking the illuminating light supply unit 30 and the control part 2 in the connected position.

By the above rotational motion of the illuminating light supply unit 30, the drive receiving projection 45a of the rotating ring 45 is pushed by the driving end 13 of one bayonet inner projection 12, causing the rotating ring 45 to rotate against the biasing force from the helical tension spring 46. As a result, the conducting brush 38b approaches the contacts 38a of the switch 38. However, in this state, the conducting brush 38b has not yet contacted the contacts 38a. Therefore, the switch 38 is still OFF, and the light source lamp 32 is in the OFF state.

Figure 11:
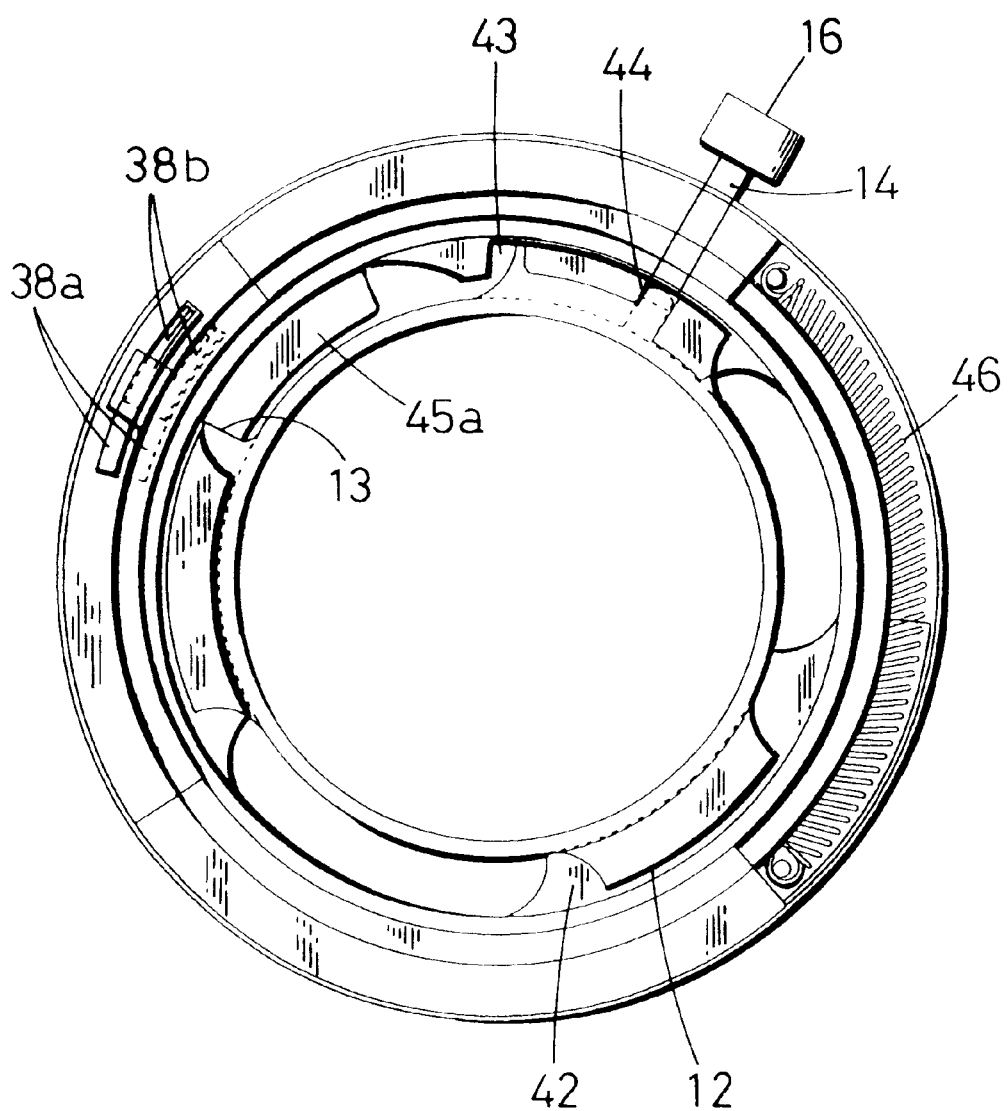
FIG. 11 is a partly-cutaway front view showing the bayonet mount is in an engaged position in a switch-ON state in the first embodiment of the present invention.

In this state, the lock pin 14 is disengaged from the first lock groove 43 by pushing the lock button 16, and the illuminating light supply unit 30 is further rotated. Consequently, the lock pin 14 engages in the second lock groove 44, as shown in FIG. 11.

In this state, the bayonet inner projections 12 are completely engaged with the rear sides of the corresponding bayonet outer projections 42, and thus the illuminating light supply unit 30 is firmly connected to the control part 2.

The drive receiving projection 45a of the rotating ring 45 is pushed by the driving end 13 of one bayonet inner projection 12, causing the rotating ring 45 to further rotate to reach a state where the conducting brush 38b contacts the contacts 38a of the switch 38. Accordingly, the switch 38 is turned ON to light the light source lamp 32, thus enabling an endoscopy.

In an interval between endoscopic inspections, the lock button 16 is pushed, and the illuminating light supply unit 30 is returned to the position where the lock pin 14 engages in the first lock groove 43, as shown in FIG. 10. Consequently, the switch 38 is turned OFF with the illuminating light supply unit 30 kept connected to the control part 2. Thus, the light source lamp 32 can be turned OFF.

By detaching the illuminating light supply unit 30 from the control part 2 upon completion of the endoscopy, the switch 38 is invariably turned OFF, and the light source lamp 32 is put out. Therefore, a waste of electric power from the battery 100 can be surely prevented.

Figure 12:
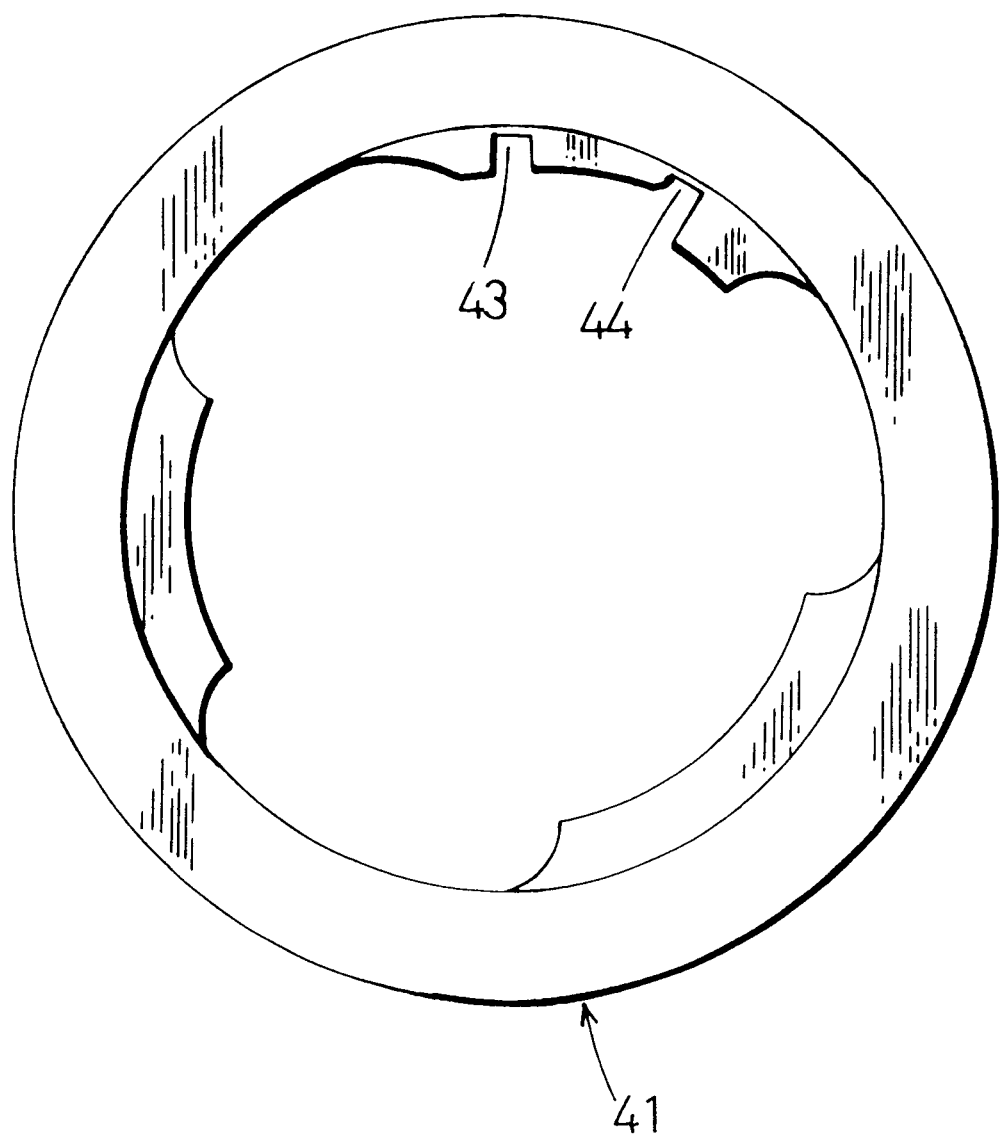
FIG. 12 is a front view showing a modified example of a bayonet mount plate in the first embodiment of the present invention.

The bayonet mount plate 41 may be modified as follows: As shown in FIG. 12, a wall surface of the bayonet mount plate 41 which is adjacent to the second lock groove 44 is slightly reduced in height from the bottom of the groove 44. By doing so, the switch-ON lock state can be readily canceled by only slightly pushing the lock button 16.

By forming the contacts 38a from an electric resistor, the switch 38 may be arranged in the form of a controller-type switch in which the electric resistance gradually increases as the switch 38 is moved from an ON position toward an OFF position. Use of such a controller-type switch enables the brightness of light emitted from the light source lamp 32 to be adjusted as desired.

Figure 13:
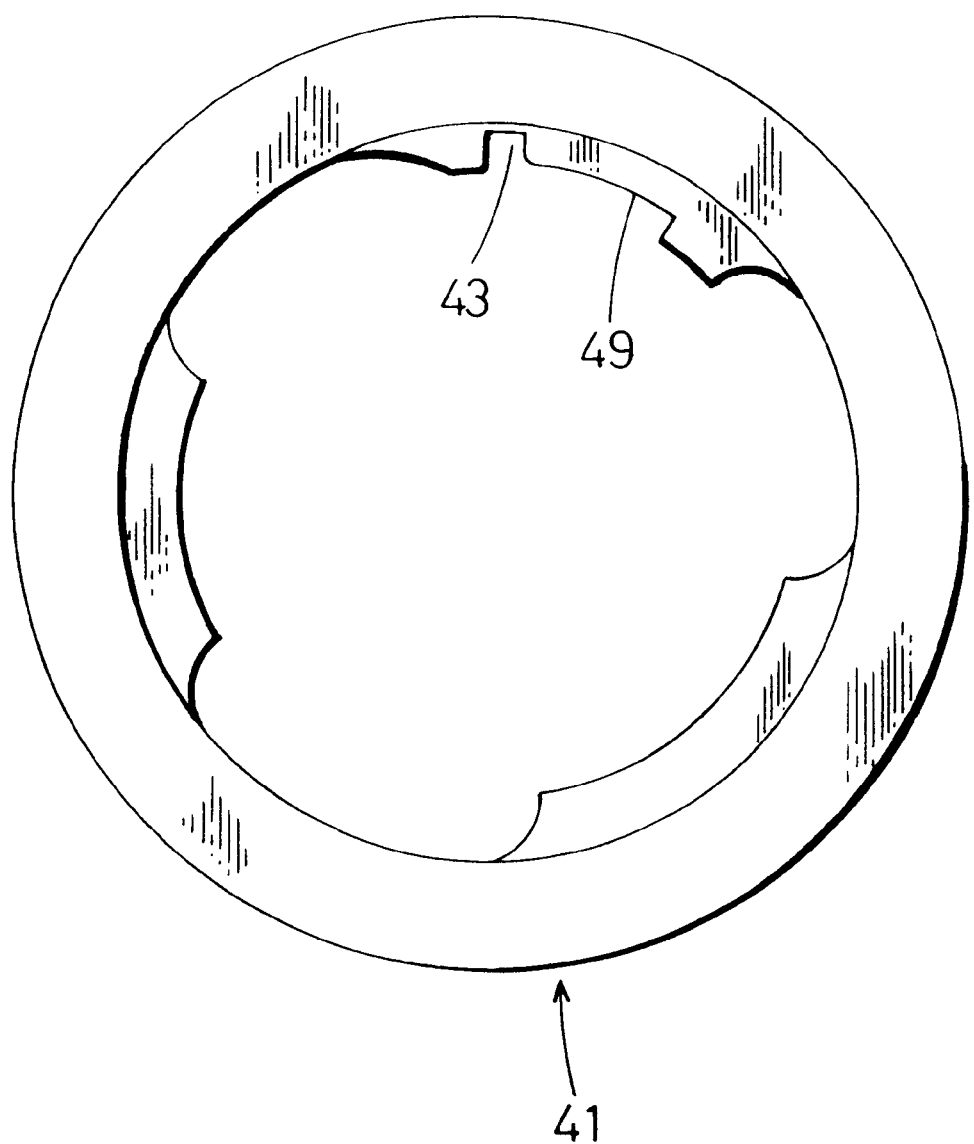
FIG. 13 is a front view of a bayonet mount plate in the first embodiment of the present invention in a case where a controller-type switch is used.

In such a case, however, the conducting brush 38b is necessary to stop at a desired position where it is in contact with the contacts 38a. Therefore, the bayonet mount plate 41 should preferably be arranged as shown, for example, in FIG. 13. That is, the bayonet mount plate 41 is not provided with the second lock groove 44, but a wall surface 49 is formed at the far side of the first lock groove 43 so that the lock pin 14 is pressed against the wall surface 49 by the biasing force from the helical compression spring 15.

By doing so, the illuminating light supply unit 30 can be stopped from rotating by frictional resistance at a desired position in a range where the conducting brush 38b is in contact with the contacts 38a. Application of such frictional resistance can be realized by using an appropriate device, e.g. an O-ring, a bayonet mount pressing spring, etc.

According to the present invention, a switch which is provided in a mechanism for connecting the endoscope control part and the illuminating light supply unit is turned ON by connecting the illuminating light supply unit to the control part in a predetermined state. The switch is turned OFF by detaching the illuminating light supply unit from the control part. Therefore, when the illuminating light supply unit is detached from the control part, the light source lamp is always turned OFF. Accordingly, a waste of power from the power supply can be surely prevented.

If a controller-type switch in which the electric resistance gradually increases as the switch is moved from an ON position toward an OFF position is used as a switch for the light source lamp, the brightness of light emitted from the light source lamp can be adjusted as desired.

Figure 14:
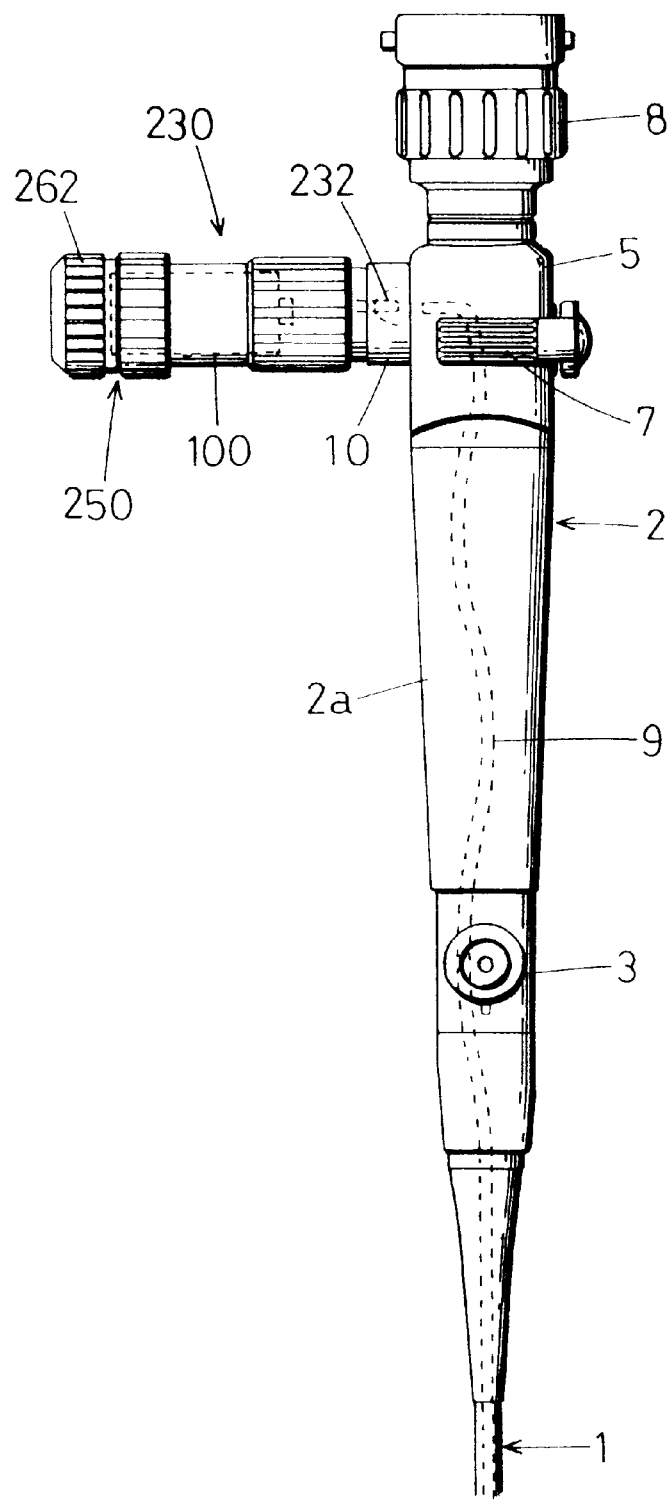
FIG. 14 is a rear view of a portable endoscope according to a second embodiment of the present invention.

FIGS. 14 to 17 show a second embodiment of the present invention. The arrangement of the control part 2 is the same as that in the first embodiment. As shown In FIG. 14, an illuminating light supply unit 230 is connected by thread engagement to a connecting ring 10 which projects from the control part 2.

The illuminating light supply unit 230 contains a light source lamp 232 that emits illuminating light which is to be supplied to the light guide fiber bundle 9, and a battery 100 or the like which serves as a power supply for lighting the light source lamp 232.

A miniature bulb with a convex lens is used as the light source lamp 232. The battery 100 may be any type of battery, e.g. a dry battery (primary battery) or a nickel-cadmium battery, which is a rechargeable secondary battery.

The battery 100 can be replaced by removing a cap 250 which is detachably attached to the outer end of the illuminating light supply unit 230. An AC/DC adapter for converting an alternating current to a direct current may be connected to the illuminating light supply unit 230 in place of the battery 100.

Figure 15:
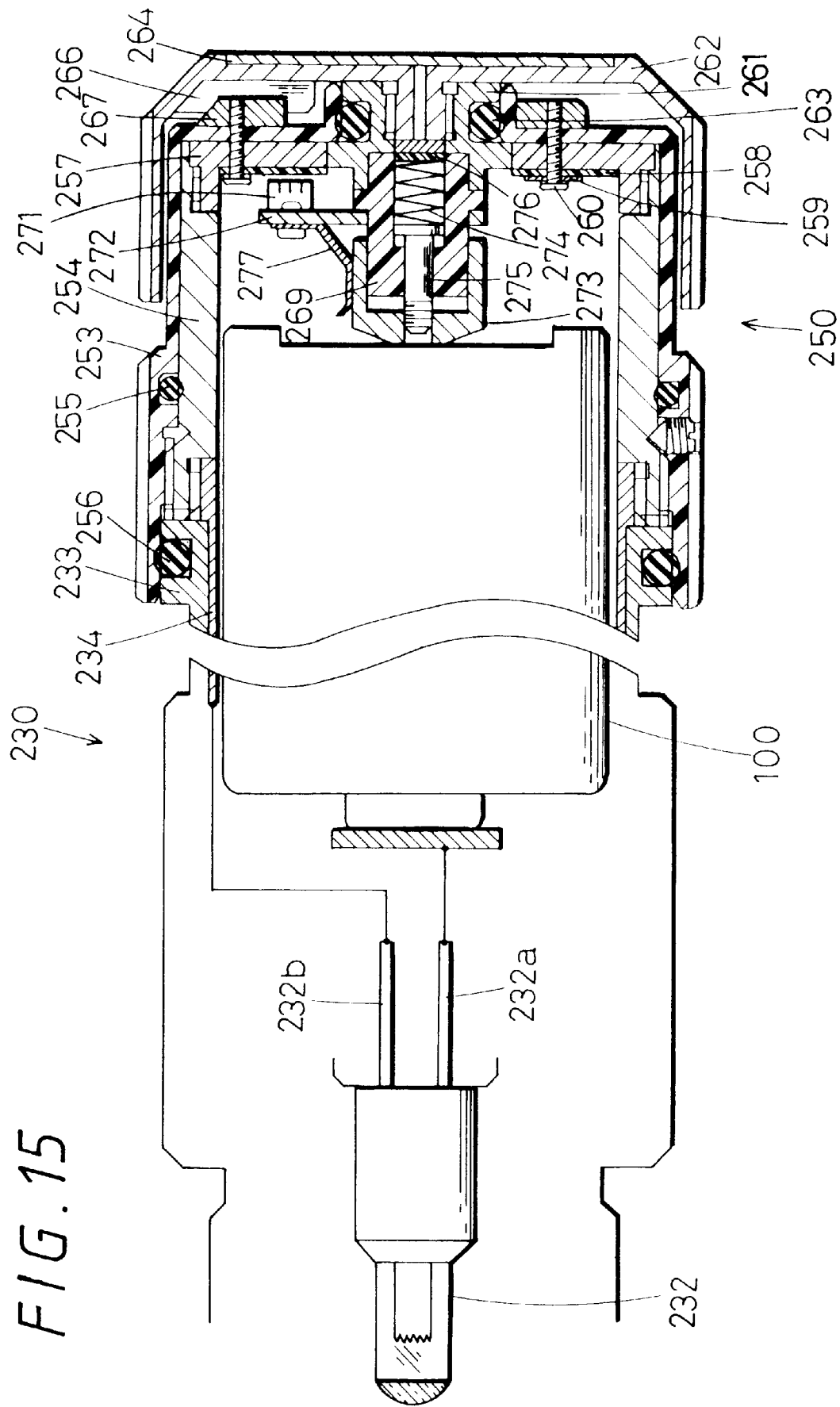
FIG. 15 is a sectional side view showing an illuminating light supply unit in the second embodiment of the present invention with a part of the supply unit omitted.

FIG. 15 shows the illuminating light supply unit 230. In the figure, illustration of an intermediate portion (battery chamber) of the unit 230 which accommodates the battery 100 is omitted, and the distal end portion of the unit 230, which is closer to the control part 2, is schematically shown by the outlines. The end portion of the illuminating light supply unit 230 which is closer to the cap 250 is illustrated in detail in a sectional view.

A first electrode 232a of the light source lamp 232 is electrically connected to the positive electrode of the battery 100 at all times. The battery chamber is formed by an outer casing 233 and an inner casing 234. The outer casing 233 is made of a material of good corrosion resistance. The inner casing 234 is made of a metallic material of good electrical conductivity.

The cap 250 incorporates a rotary switch for ON/OFF controlling the supply of electric power from the battery 100 to the light source lamp 232 to turn ON/OFF the light source lamp 232.

An outer cylinder 253, which is made of a material of good corrosion resistance, forms the outer wall of the cap 250. An inner cylinder 254, which is made of a metal of good electrical conductivity, is disposed inside the outer cylinder 253 in contact with the inner peripheral surface of the outer cylinder 253. The inner cylinder 254 is detachably thread-engaged with the inner casing 234 of the battery chamber. The outer cylinder 253 and the inner cylinder 254 are integrated together by thread engagement and bonding. Reference numeral 255 denotes an O-ring for sealing.

Further, a sealing O-ring 256 is disposed in the area of fit between the outer peripheral surface of the battery chamber-side end portion of the outer casing 233 and the inner peripheral surface of the outer cylinder 253, thereby preventing water from entering the inside of the cap 250 through the area of fit therebetween.

A cap body 257, which is made of a metal of good electrical conductivity, is integrally connected to the other end portion of the inner cylinder 254 at the inner side of the outer cylinder 253 by thread engagement and bonding. An electrically insulating base 258 is provided on the inner end surface of the cap body 257, and an electric-resistance contact piece 259 is mounted on the base 258. The cap body 257 and the electric-resistance contact piece 259 are electrically connected through a fixing screw 260.

Figure 16:
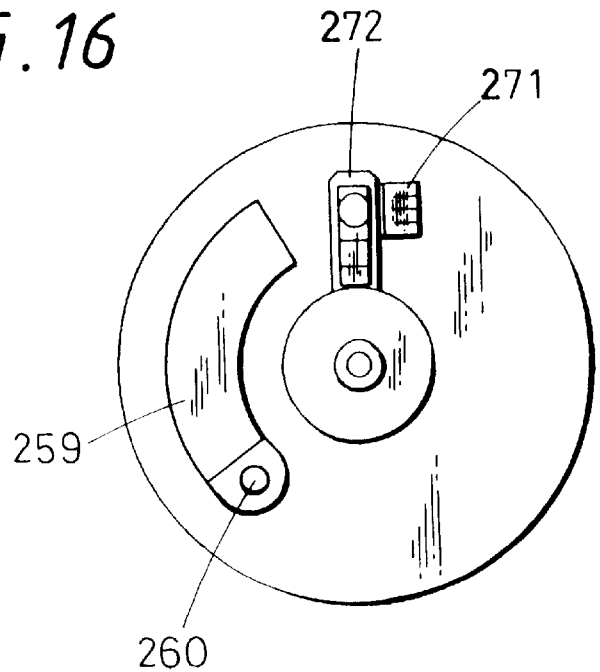
FIG. 16 is a front view showing a switch portion in an OFF state in the second embodiment of the present invention.

As a result, the electric-resistance contact piece 259 is electrically connected at all times to a second electrode 232b of the light source lamp 232 through the fixing screw 260, the cap body 257, the inner cylinder 254, and the inner casing 234. It should be noted that, as shown in FIG. 16, the electric-resistance contact piece 259 is formed and disposed in the shape of a circular arc centered at the axis of the illuminating light supply unit 230.

A rotating shaft 261 is fitted in the center of the projecting end portion of the outer cylinder 253 so as to be rotatable about the axis of the illuminating light supply unit 230. A switch control ring 262 is integrally connected to the outer end portion of the rotating shaft 261 by thread engagement and bonding. The switch control ring 262 has a substantially bowl-like configuration, and is disposed so as to surround the end portion of the cap 250. Reference numeral 263 denotes an O-ring for sealing, and 264 denotes a decorative plate.

The switch control ring 262 is rotatable about the axis of the illuminating light supply unit 230, but the rotation of the switch control ring 262 is restricted within a predetermined range by contact between a stopper 266 which projects from the inner surface of the switch control ring 262 and a stopper 267 which is screwed to both the cap body 257 and the outer cylinder 253.

The ring diameter of the O-ring 263, which is fitted around the rotating portion of the switch control ring 262, is smaller than that of the O-ring 256, which is fitted around the rotating portion of the outer cylinder 253. Accordingly, resistance to the rotational motion at the area of fit is lower at the O-ring 263 than at the O-ring 256. Therefore, when the switch control ring 262 is rotated within a predetermined range, the outer cylinder 253, the inner cylinder 254, or the cap body 257 does not rotate.

An electrically insulating shaft 269 is integrally bonded to the inner end of the rotating shaft 261. A brush holder 272 of good electrical conductivity projects sidewardly from the insulating shaft 269. A conducting brush 271 (conducting contact piece) of good electrical conductivity is secured to the brush holder 272 to face the base 258.

As a result, when the switch control ring 262 is rotated within a predetermined range which is limited by the stoppers 266 and 267, the conducting brush 271 rotates about the axis of the illuminating light supply unit 230 together with the switch control ring 262. Thus, it is possible to attain an ON state where the conducting brush 271 is in contact with the electric-resistance contact piece 259, and an OFF state where the conducting brush 271 is out of contact with the electric-resistance contact piece 259. The switching operation will be described later.

A movable contact 273 is provided on the inner end portion of the insulating shaft 269, and pressed against the negative electrode of the battery 100 by biasing force from a helical compression spring 274. A push rod 275 is interposed between the helical compression spring 274 and the movable contact 273. Reference numeral 276 denotes an electrical insulator.

A resilient conducting contact piece 277 is secured at its proximal portion to the brush holder 272. The distal end portion of the conducting contact piece 277 is resiliently pressed on the outer peripheral surface of the movable contact 273. As a result, the conducting brush 271 is electrically connected at all times to the negative electrode of the battery 100 through the brush holder 272, the conducting contact piece 277, and the movable contact 273.

Figure 17:
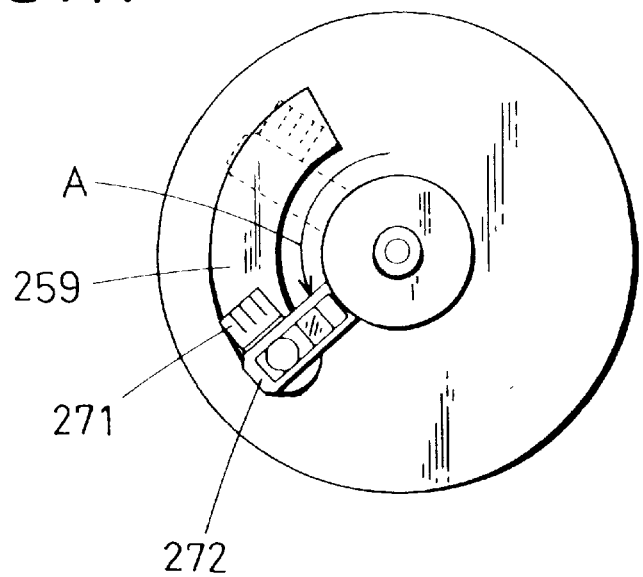
FIG. 17 is a front view showing the switch portion in an ON state in the second embodiment of the present invention.

FIGS. 16 and 17 show the positional relationship between the conducting brush 271 and the electric-resistance contact piece 259 at two extremities of the rotation range when the switch control ring 262 is rotated. In the state shown in FIG. 16, the conducting brush 271 and the electric-resistance contact piece 259 are separate from each other. Therefore, the relationship between the negative electrode of the battery 100 and the second electrode 232b of the light source lamp 232 is cut OFF at the switch. Accordingly, the illuminating light supply unit 230 is in a switch-OFF state, and the light source lamp 232 is in an OFF state.

In the state shown in FIG. 17, the conducting brush 271 is in electrical contact with the electric-resistance contact piece 259 at a position near the fixing screw 260. Therefore, the negative electrode of the battery 100 and the second electrode 232b of the light source lamp 232 are electrically connected with substantially no voltage drop therebetween. Accordingly, the illuminating light supply unit 230 is in a switch-ON state, and the light source lamp 232 is lit up.

However, when the switch moves from the OFF (lamp-OFF) position to the ON (lamp-ON) position, the conducting brush 271 first comes in contact with the electric-resistance contact piece 259 at a position away from the fixing screw 260, as shown by the dashed line in FIG. 17. Then, the conducting brush 271 gradually approaches the fixing screw 260 by rotating as shown by the arrow A.

Accordingly, the switch does not suddenly enter an ON state from an OFF state, but first goes into a state where all the electric resistance of the electric-resistance contact piece 259 is inserted between the negative electrode of the battery 100 and the second electrode 232b of the light source lamp 232, and after the electric resistance has gradually decreased, the switch reaches an ON position as shown by the continuous line in FIG. 17.

As a result, the inrush current flowing when the light source lamp 232 is turned ON is reduced, and thus the lifetime of the light source lamp 232 can be increased. If the switch control ring 262 is stopped at a position where the conducting brush 271 contacts an intermediate portion of the electric-resistance contact piece 259, the brightness of light emitted from the light source lamp 232 can be adjusted as desired by a voltage drop across the electric-resistance contact piece 259.

It should be noted that the present invention is not necessarily limited to the above-described embodiments, but may also be applied to a system in which an AC/DC adapter is used as a power supply in place of the battery 100.

According to the present invention, when a switch for turning ON/OFF a light source lamp is moved from a lamp-OFF position to a lamp-ON position, the electric resistance between the light source lamp and the power supply therefor gradually decreases from a high-resistance state to a low-resistance state. Therefore, the inrush current flowing when the light source lamp is turned ON is reduced, and thus, the lifetime of the light source lamp can be increased. If the switch is stopped at a position where the electric resistance is an intermediate level, the brightness of light emitted from the light source lamp can be adjusted as desired. The present invention can be realized simply by adding an electric resistor to the switch, with substantially no increase in the overall size of the illuminating light supply unit. Therefore, the illuminating light supply unit as attached to the endoscope control part will not degrade the controllability of the portable endoscope.

While the invention has been described by reference to specific embodiments chosen for purposes of illustration, it should be apparent that numerous modifications could be made thereto by those skilled in the art without departing from the basic concept and scope of the invention.

We claim:

1. A portable endoscope having a control part containing an entrance end portion of a light guide for transmitting light for illuminating an object, and an illuminating light supply unit containing a light source lamp for supplying illuminating light to said light guide, said portable endoscope comprising:

a bayonet mount that detachably connects said control part and said illuminating light supply unit; and a switch that turns ON/OFF said light source lamp, said switch being provided in said bayonet mount;

wherein, said switch is turned ON when said illuminating light supply unit is connected to said control part in a predetermined state, whereas, said switch is turned OFF when said illuminating light supply unit is detached from said control part, said switch being in an OFF condition when said illuminating light supply unit is connected to said control part in a first state, said switch being in an ON condition when said illuminating light supply unit is connected to said control part in a second state.

2. A portable endoscope according to claim 1, wherein said first state lies between said second state and a state where said bayonet mount is disengaged.

3. A portable endoscope according to claim 1, further comprising a releasable lock mechanism that locks each of said first state and said second state.

4. The portable endoscope of claim 1, wherein said switch includes contacts disposed in said bayonet mount.

5. The portable endoscope of claim 1, wherein said illuminating light supply unit accommodates at least one of a dry battery and a rechargeable battery as a power supply for lighting said light source lamp.

6. The portable endoscope of claim 1, further comprising:

a power supply that supplies electrical power to said light source lamp, said power supply comprising an AC/DC adapter that converts an alternating current to a direct current.

7. A portable endoscope having a control part containing an entrance end portion of a light guide that transmits light to illuminate an object, and an illuminating light supply unit containing a light source lamp that supplies illuminating light to said light guide, said portable endoscope comprising:

a connecting mechanism that detachably connects said control part and said illuminating light supply unit; and a switch that turns ON/OFF said light source lamp, said switch being provided in said connecting mechanism, wherein said switch is turned ON when said illuminating light supply unit is connected to said control part in a predetermined state, whereas, said switch is turned OFF when said illuminating light supply unit is detached from said control part, said switch being in an OFF condition when said illuminating light supply unit is connected to said control part in a first state, said switch being in an ON condition when said illuminating light supply unit is connected to said control part in a second state.

8. The portable endoscope of claim 7, wherein said first state lies between said second state and a state where said connecting mechanism is disengaged.

9. The portable endoscope of claim 7, further comprising a lock mechanism that releasably locks each of said first state and said second state.

10. A portable endoscope having a control part containing an entrance end portion of a light guide for transmitting light for illuminating an object, and an illuminating light supply unit containing a light source lamp for supplying illuminating light to said light guide, said portable endoscope comprising:

means for selectively connecting said control part to said illuminating light supply unit; and means for selectively activating said light source lamp, said selective activating means being associated with said selective connecting means, wherein said selective activating means is activated when said illuminating light supply unit is connected to said control part in a predetermined state, said selective activating means being de-activated when said illuminating light supply unit is detached from said control part, said selective activating means also being de-activated when said illuminating light supply unit is connected to said control part in a first state, said selective activating means being activated when said illuminating light supply unit is connected to said control part in a second state.

\* \* \* \* \*